US007005527B2

(12) United States Patent
Szabo et al.

(10) Patent No.: US 7,005,527 B2
(45) Date of Patent: Feb. 28, 2006

(54) PROCESS FOR THE PRODUCTION OF BERAPROST AND ITS SALTS

(75) Inventors: Tibor Szabo, Budapest (HU); Jozsef Bodi, Budapest (HU); Gyuia Dalmadi, Budapest (HU); Zsusanna Baloghnekardos, Budapest (HU); Zoltan Szevfrenyi, Budapest (HU)

(73) Assignee: Chinoin Gyogyszer es Vegyeszeti Termekek Gyara Rt., Budapest (HU)

( * ) Notice: Subject to any disclaimer, the term of this patent is extended or adjusted under 35 U.S.C. 154(b) by 63 days.

(21) Appl. No.: 10/484,209

(22) PCT Filed: Jul. 25, 2002

(86) PCT No.: PCT/HU02/00074

§ 371 (c)(1),
(2), (4) Date: Apr. 1, 2004

(87) PCT Pub. No.: WO03/011849

PCT Pub. Date: Feb. 13, 2003

(65) Prior Publication Data

US 2004/0209945 A1   Oct. 21, 2004

(30) Foreign Application Priority Data

Jul. 30, 2001   (HU) .................... 0103089

(51) Int. Cl.
   *C07D 307/93*   (2006.01)
(52) U.S. Cl. .................... 549/214; 549/458; 549/214
(58) Field of Classification Search ............... 549/458, 549/214
   See application file for complete search history.

(56) References Cited

FOREIGN PATENT DOCUMENTS

| EP | 0 024 943 A | 3/1981 |
|---|---|---|
| EP | 0 084 856 A1 | 8/1983 |
| JP | 3-69909 B2 | 11/1991 |

OTHER PUBLICATIONS

Bruce E. Maryanoff et al.; Chem. Rev.; vol. 89, pp. 863-927, 1989.

Hisanori Wakita et al.; Tetrahedron; vol. 55, pp. 2449-2474, 1999.
Silylating Agents, Fluka Chemie AG, Second Edition, 1995, pp. 1-100.
Wakita et al., Tetrahedron, vol. 55, pp. 2449-2474 (1999).
Chandrasekhar et al., J. Org. Chem., vol. 62, No., 8, pp. 2628-2629 (1997).
Rodriguez et al., Tetrahedron Letters, vol. 40, pp. 5161-5164 (1999).
Cossy, Tetrahedron Letters, vol. 30, No. 31, pp. 4113-4116 (1989).
Blaser et al., Helv. Chim. Acta., vol. 74, No. 1, pp. 141-145 (1991).
Mahrwald et al., J. Prakt. Chem., vol. 328, No. 576, pp. 777-783 (1986).
Tolstikov et al., J. Org. Chem., vol. 28, No. 4.1, pp. 543-552 (1992).
Roland et al., Bull. Soc. Chim. Fr., vol. 133, No. 11, pp. 1149-1154 (1996).

*Primary Examiner*—Cecilia Tsang
*Assistant Examiner*—Niloofar Rahmani
(74) *Attorney, Agent, or Firm*—Birch, Stewart, Kolasch & Birch, LLP

(57) ABSTRACT

The present invention relates to a new process for the preparation of beraprost of formula (I) using new intermediates.

15 Claims, 4 Drawing Sheets

(III)   Figure 3

(VII)  Figure 7

(VIII)  Figure 8

(IX)  Figure 9

PROCESS FOR THE PRODUCTION OF BERAPROST AND ITS SALTS

The present invention relates to a new synthesis of the beraprost of the formula (I) and its salts and to the new intermediates of the general formulas (IV), (V) and (VI) —wherein $R^1$ stands for methyl of ethyl groups, $R^2$ stands for a straight or branched alkyl group containing 1–4 carbon atoms—which are used in the new synthesis.

Figure 1:
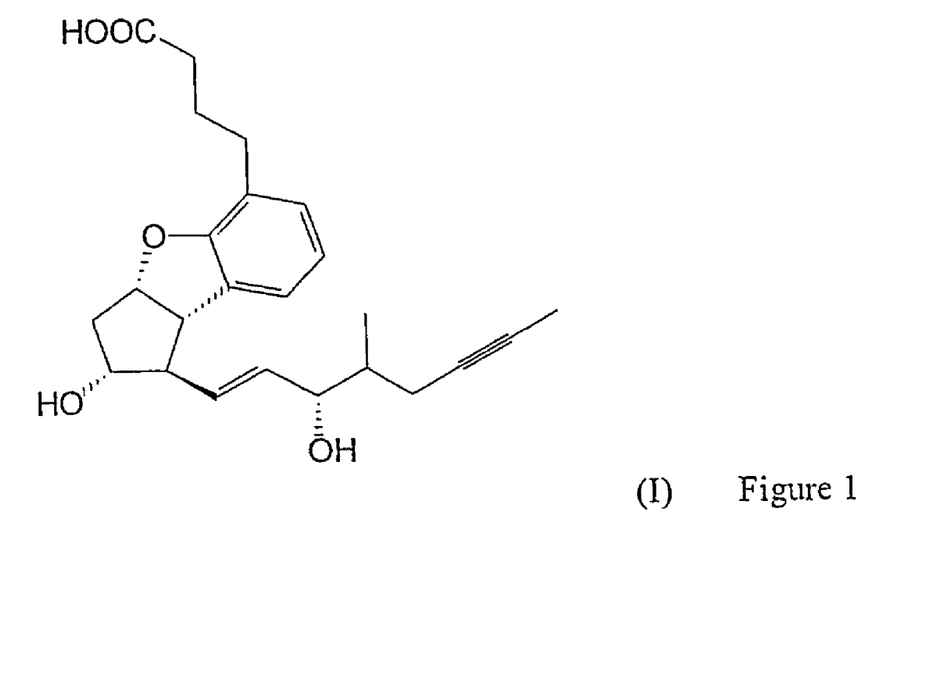
FIGS. 1,2,3,4,5,6,7,8 and 9 show general formulas (I), (II), (III), (IV), (V), (VI), (VII), (VIII) and (IX).

The salts of beraprost of the formula (I), especially the sodium salt are orally applicable prostacycline derivatives, which are effectively applicable for the treatment of chronic peripheral vascular disease, arterial thrombosis and the pulmonary hypertension. The active pharmaceutical ingredient of the formula (I) and its salts used in the commercial pharmaceutical compositions are racemic compounds containing four stereoisomers. The synthesis of the compound of formula (I) and its salts is described in European Patent Application Publ. No 084856A, in the published Japanese Patent Application No 59-34787A and in Tetrahedron, 55, p 2449–2474 (1999) and the summary of the synthesis is shown by Scheme 1. The meaning of TBDMS is tert.butyl-dimethylsilyl group, Ac means acetyl group, W-H-E reaction means Wittig-Horner-Emmon's reaction in Scheme 1. From the Scheme 1 and from the prior art it can be seen that the synthetic route belonging to the state of the art is rather long and its yields are moderate.

The object of this invention is to provide a shorter synthesis with higher yield. Unexpectedly it was found that the protection of the primary hydroxy group by an acid sensitive protecting group and the protection of the secondary hydroxy group by a base sensitive protecting group and the subsequent removal of the protecting group from the primary hydroxy group may be avoided by the use of a single specially selected protective group, which makes possible at the same time the selective oxidation.

The removal of above protective group before the reduction of the oxo-group at the 15-position and the careful selection of the reducing agent increase the stereoselectivity of the reduction and the yield of the entire synthesis.

Figure 7:
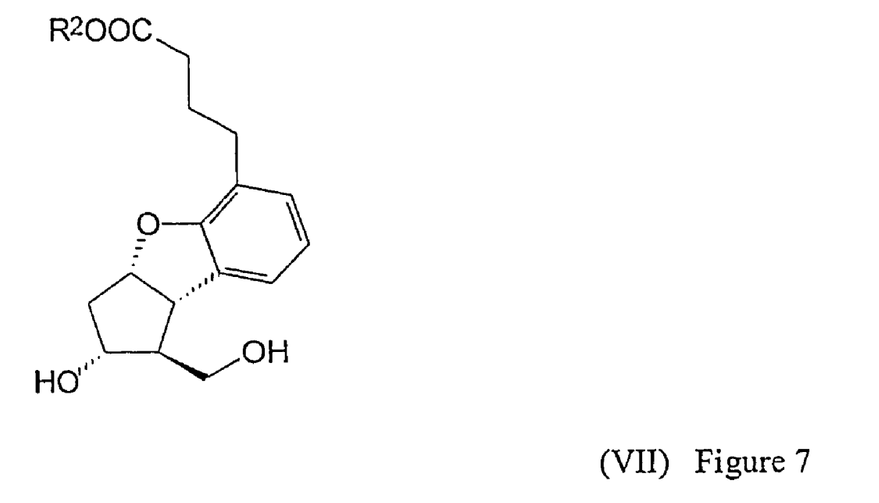
Figure 8:
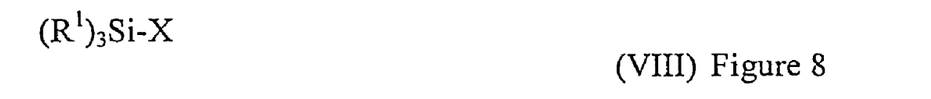

According to the present invention a compound of the general formula (VII)—wherein $R^2$ means a straight or branched alkyl group containing 1–4 carbon atoms—is reacted with a compound of the general formula (VIII) —wherein $R^1$ means a methyl or an ethyl group, X stands for chlorine or bromine or iodine atom,

$CF_3SO_2$—O-group, azido-, cyano-, or group or a further group such as acetamido or Acetyloxy as described in following literature:

Silylating Agents, Fluka Chemie AG, Second Edition, Edited by Dr. Gert van Look (1995) ISBN 3-905617-080—is reacted, the obtained compound of the general formula (VI)—wherein the meanings of $R^1$ and $R^2$ are as defined above—is oxidized into the aldehyde of the general formula (V)—wherein the meanings of $R^1$ and $R^2$ are as defined above—the obtained above aldehyde with or without isolation is reacted with a phosphonate of the general formula (IX)—wherein $R^3$ stands for straight or branched alkyl group containing 1–4 carbon atoms the obtained compound of the general formula (IV)—wherein the meanings of $R^1$ and $R^2$ are as defined above—is deprotected by the splitting off the protecting group at the position 11 and the compound of the general formula (III)—wherein the meaning of $R^2$ is as defined above—thus obtained is reduced, the obtained compound of the general formula (II)—wherein the meaning of $R^2$ is as defined above—is hydrolized and the acid of the formula (I) is isolated and with reaction of a base it is transformed into its salt and the salt is isolated or the obtained acid of the formula (I) is transformed without isolation into its salt and the salt thus obtained is isolated.

During the above process a compound of the general formula (VII) is reacted with a compound of the general formula (VIII) suitable for the introducing of the triethylsilyl or trimethylsilyl group—wherein $R^1$ means methyl or ethyl group, X stands for chlorine, bromine, iodine atom, $CF_3$—$SO_2$—O—, azido-, cyano- or group or a further group such as acetamido or acetyloxy as described in the following literature: Silylating Agents, Fluka Chemie AG, Second Edition, Edited by Dr. Gert. Van Look (1995) ISBN 3-905617-080—trimethylsilyl or triethylsilyl halogenides are preferred, especially the chlorides or the specific derivatives listed above. The received disilylated diols of the general formula (VI) may be oxidized most advantageously by a mixture of dimethylsulfoxide, oxalyl-chloride and triethylamine into the aldehydes of the general formula (V).

Figure 3:
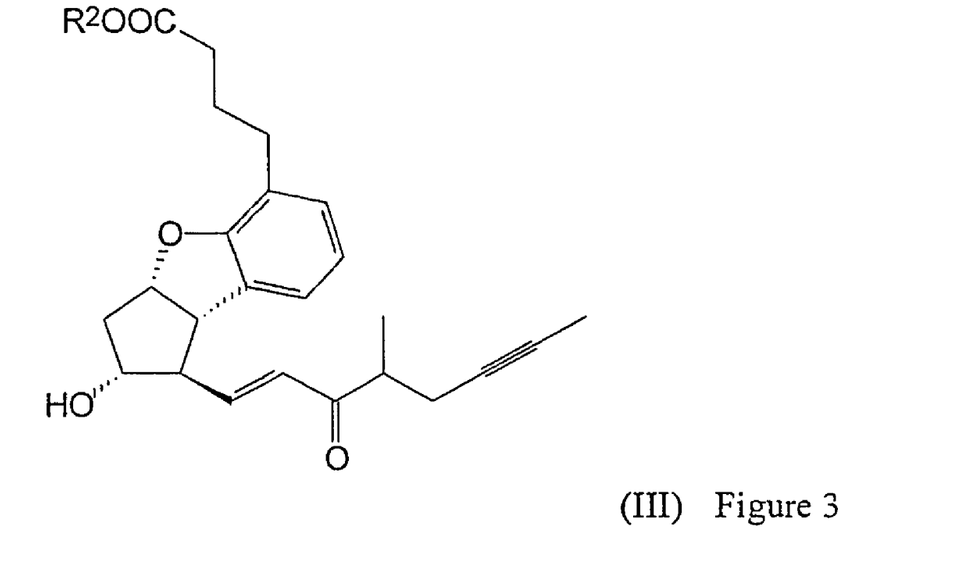
Figure 4:
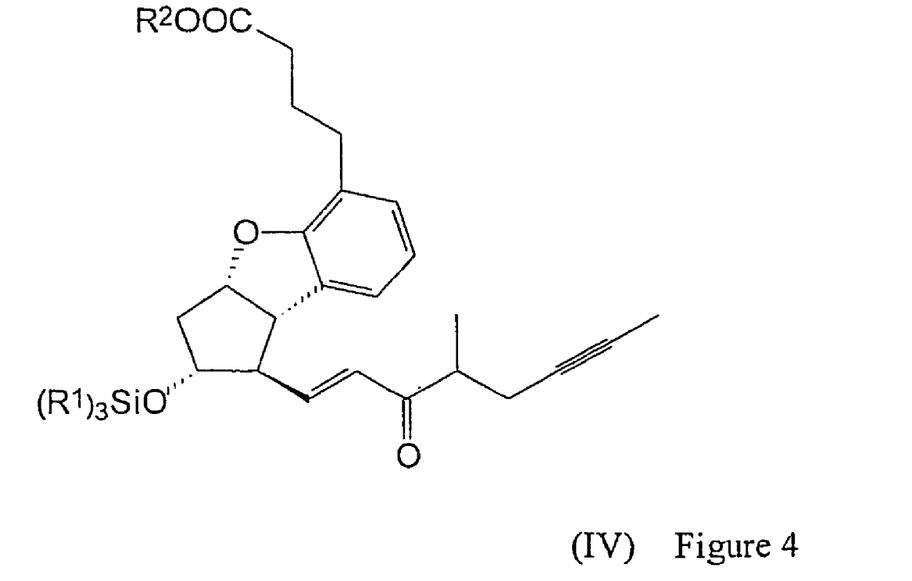
Figure 5:
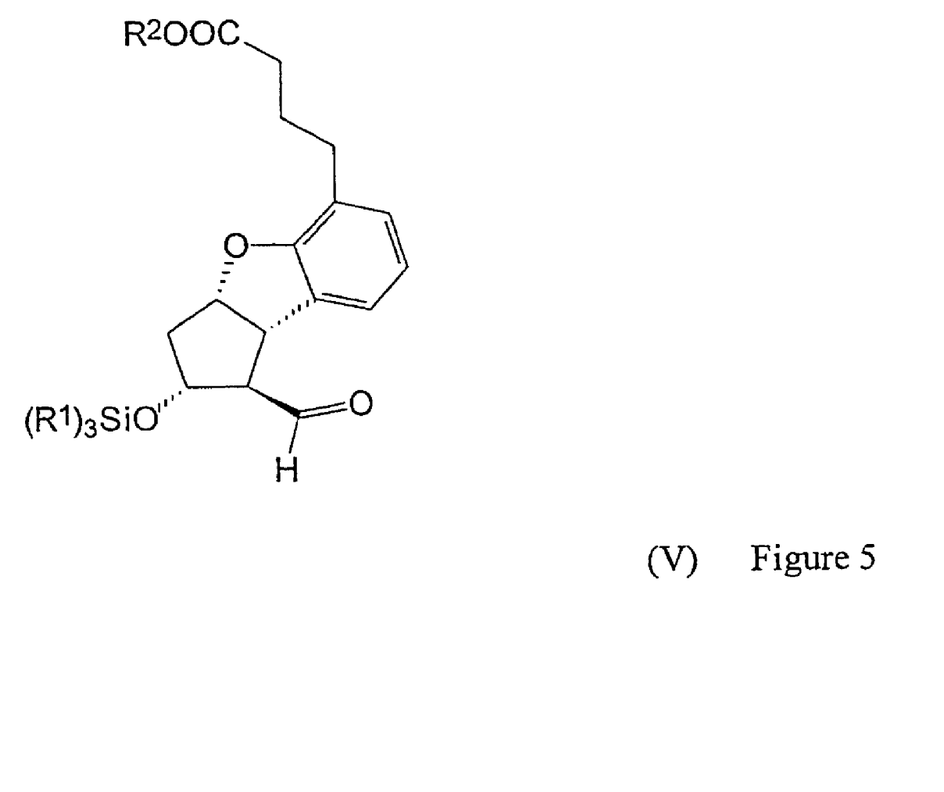
Figure 6:
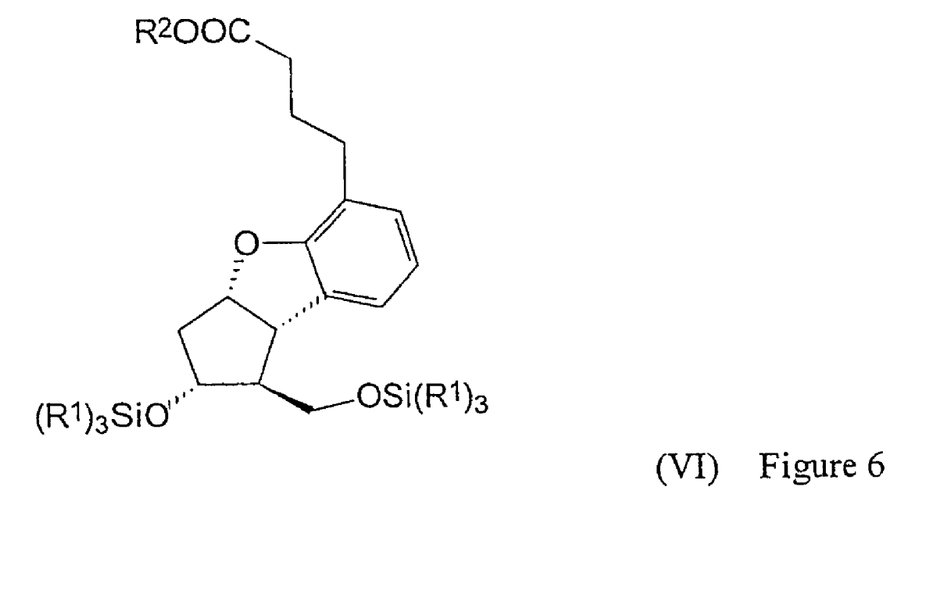

After splitting off the triethylsilyl or trimethylsilyl protective group of the secondary hydroxy-group at the compounds of the general formula (IV) in acidic medium we obtain the enon type compounds of the general formula (III).

Figure 2:
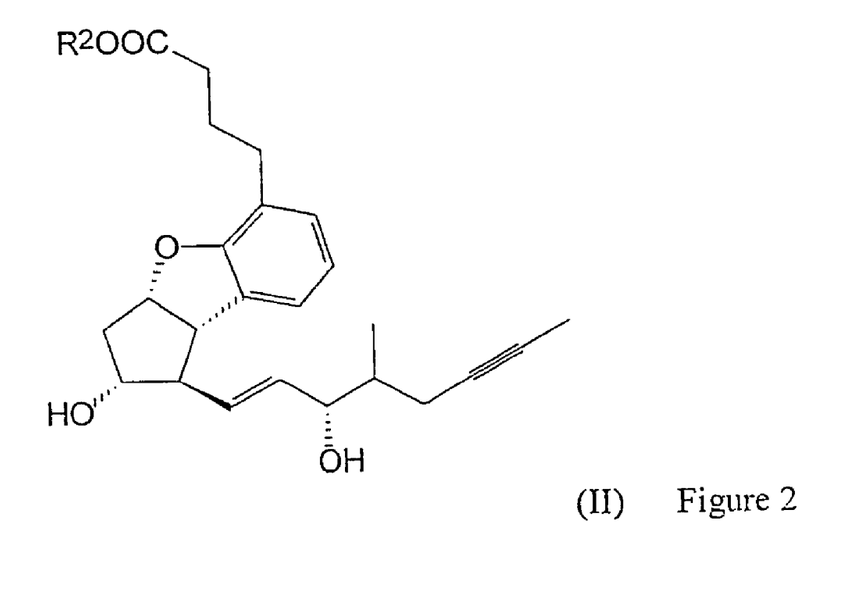

The stereoselective reduction of compounds of the general formula (III) is carried out preferably by using diisobu-tylaluminium-2,6-di-tert.butyl-4-methylphenoxide and the compounds of the formula (II) are obtained the hydrolysis of which in basic medium leads to the beraprost of the formula (I). The salts of compound of the formula (I) can be produced by reacting it with bases. Salt-formation can be carried out after isolation of beraprost of formula (I) with or without its isolation.

For preparation of beraprost sodium salt the use of sodium hydroxide is the most preferred as a base.

Figure 9:
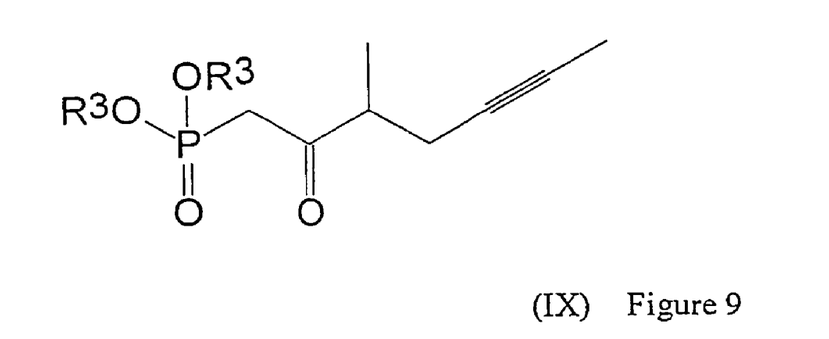

Compounds of the general formula (VII) and phosphonates of the general formula (IX) used in the process of the present invention may be prepared as described for example in Tetrahedron 55 p 2449–2474 (1999). Compounds of the general formula (VIII) are commercially available compounds.

The present invention will be described in more detail by way of the following examples without limiting our claims thereto.

EXAMPLE 1

The Compound of the General Formula (VI)—wherein $R^1$ Stands for Ethyl Group and $R^2$ Stands for Methyl Group 1.84 g (6 mmol) of diol of the general formula (VII)—wherein $R^2$ means a methyl group—is dissolved in 10 ml of pyridine. The solution is stirred and 2.35 ml (14 mmol) of triethylsilyl chloride is added. Stirring is continued for 30 minutes and then the reaction mixture is poured into the mixture of 50 ml of water and 20 ml of hexane. The aqueous phase is extracted with hexane (2×10 ml) and the combined hexane solution is washed with 30 ml of 1 M aqueous solution of $NaHSO_4$, 30 ml of water, 30 ml 1 M $NaHCO_3$ solution, 2×30 ml of water, then with saturated NaCl solution. The hexane solution is dried on $Na_2SO_4$ for one hour and then it is evaporated. The above mentioned title compound is obtained as colourless oil.

Yield: 3.08 g (96%).

TLC-$R_f$ (hexane-ethylacetate 3:1)=0.60, (TLC=Thin-layer-chromatography)

TLC-$R_f$ (hexane-ethylacetate 10:1)=0.32.

$^1$H NMR (400 MHz, $C_6D_6$), δH (ppm): 0.54q, 0.63q [12H; J=7.9 Hz; Si(C$\underline{H}_2$CH$_3$)$_3$]; 0.95t, 1.02t [18H; J=7.9 Hz; Si(CH$_2$C$\underline{H}_3$)$_3$]; 2.05m, 2.06m [3H; 10-H, 3-H$_2$]; 2.16m, 2.22m, 2.25m [4H; 12-H, 2-H$_2$, 10-H]; 2.70m [2H; 4-H$_2$]; 3.32s [3H; OCH$_3$]; 3.51dd [1H; J=8.8,7.0 Hz; 8-H]; 3.63m [2H; 13-H$_2$]; 4.01td [1H; J=7.4,5.8 Hz; 11-H]; 4.85ddd [1H; J=9.1,7.2,5.4 Hz; 9-H]; 6.85t [1H; J=7.3 Hz; 2'-H]; 6.93d [1H; J=7.3 Hz; 1'-H]; 7.19d [1H; J=7.3 Hz; 3'-H] $^{13}$C NMR (100 MHz, $C_6D_6$), δC (ppm): 5.5, 5.9 [Si(C$\underline{H}_2$CH$_3$)$_3$]; 7.7, 7.8 Si(CH$_2$C$\underline{H}_3$)$_3$]; 26.1 [C-3]; 30.5 [C-4]; 34.3 [C-2]; 43.6 [C-10]; 47.9 [C-8]; 51.5 [OCH$_3$]; 59.0 [C-12]; 63.0 [C-13]; 73.6 [C-11]; 85.9 [C-9]; 121.4 [C-2']; 123.3 [C-3']; 124.3 [C-5]; 129.6 [C-1']; 132.0 [C-7]; 158.8 [C-6]; 173.9 [C-1].

EXAMPLE 2

The Compound of the General Formula (V)—wherein $R^1$ Stands for Ethyl Group $R^2$ Stands for Methyl-group 0.27 ml (3 mmol) of oxalyl-chloride is dissolved in 3 ml of dichloromethane and the mixture is cooled down to −60° C. To this solution 0.44 ml (6.2 mmol) of dimethyl sulfoxide dissolved in 3 ml dichloromethane is added dropwise at −60° C.

After stirring for 5 minutes 1.07 g (2 mmol) of compound of the general formula (VI) prepared by the Example 1 dissolved in 2 ml of dichloromethane is added to the mixture.

The mixture is let to warm up to −35° C. and it is stirred for 30 minutes at this temperature.

The reaction mixture is cooled down to −60° C. and 1.42 ml (10 mmol) of triethylamine is added. The mixture is stirred for 15 minutes and 10 ml of water and 7ml of 10 M aqueous solution of $NaHSO_4$ are added at room temperature. The aqueous phase is extracted twice with 5 ml of dichloromethane. The combined organic phase is washed with 10 ml of 1 M aqueous solution of $NaHCO_3$, with 10 ml of water and 10 ml of saturated NaCl solution.

The organic phase is dried on $Na_2SO_4$, it is evaporated in vacuum and the above mentioned title compound is obtained as a yellow oil which may be used in the next reaction step with or without purification.

Yield: 0.83 g (99%)

TLC-$R_f$ (hexane-diisopropylether 1:1)=0.44,

TLC-$R_f$ (hexane-ethylacetate 3:1)=0.52

$^1$H NMR (400 MHz, $C_6D_6$), δH (ppm): 0.41q [6H; J=8.0 Hz; Si(C$\underline{H}_2$CH$_3$)$_3$]; 0.84t [9H; J=8.0 Hz; Si(CH$_2$C$\underline{H}_3$)$_3$]; 1.94m, 2.02m [3H; 10-H, 3-H$_2$]; 2.17m, 2.20t [3H; J=7.4 Hz; 10-H, 2-H$_2$]; 2.64m [2H; 4-H$_2$]; 2.73t [1H; J=6.0 Hz; 12-H]; 3.32s [3H; OCH$_3$]; 3.73dd [1H; J=8.7,6.4 Hz; 8-H]; 4.04q [1H; J=6.0 Hz; 11-H]; 4.69m [1H; 9-H]; 6.75t [1H; J=7.4 Hz; 2'-H]; 6.88d, 6.91d [2H; J=7.4 Hz; 1'-H, 3'-H]; 9.46d [1H; J≈1 Hz; 13-H]] $^{13}$C NMR (100 MHz, $C_6D_6$), δC (ppm): 5.6 [Si(C$\underline{H}_2$CH$_3$)$_3$]; 7.5 Si(CH$_2$C$\underline{H}_3$)$_3$]; 26.0 [C-3]; 30.4 [C-4]; 34.2 [C-2]; 43.7 [C-10]; 45.9 [C-8]; 51.6 [OCH$_3$]; 68.8 [C-12]; 73.9 [C-11]; 85.7 [C-9]; 121.6 [C-2']; 123.2 [C-3']; 124.3 [C-5]; 129.9 [C-1']; 130.4 [C-7]; 158.7 [C-6]; 173.9 [C-1]; 200.6 [C-13].

EXAMPLE 3

The Compound of the General Formula (IV)—wherein $R^1$ Stands for Ethyl Group $R^2$ Stands for Methyl Group Oily dispersion of 92 mg of sodium hydride (60%) (2.3 mmol) is suspended in 2 ml of toluene and 0.51 ml (2.2 mmol) of phosphonate of the general formula (IX)—wherein $R^3$ stands for methyl group—is dissolved in 1 ml of toluene and added to the mixture at 15° C. under nitrogen atmosphere. The mixture is stirred for 20 minutes at 15° C. and then the solution containing phosphonate sodium salt is added dropwise to 0.83 g (2 mmol) of crude aldehyde of the general formula (V)—obtained according to the Example 2—dissolved in 2 ml of toluene at −10° C. After stirring for two hours 10 ml of water and 2 ml of 1 M aqueous solution of $NaHSO_4$ are added to the reaction mixture and it is stirred for two minutes. The aqueous phase is extracted twice with 5 ml of toluene and the combined toluene solution is extracted with 10 ml of water, 10 ml of 1 M aqueous solution of $NaHCO_3$, 10 ml of water and 10 ml of saturated NaCl solution.

The solution is dried on $Na_2SO_4$, it is evaporated in vacuum and the above mentioned title compound is obtained as a yellow oil, which may be used in the next reaction step without purification.

Yield: 1.2 g (>99%)

TLC-$R_f$ (hexane-diisopropyl-ether 1:1)=0.49

TLC-$R_f$ (hexane-ethylacetate 3:1)=0.54

$^1$H NMR (400 MHz, $C_6D_6$), δH (ppm): 0.47q, 0.48q [6H; J=7.8 Hz; Si(C$\underline{H}_2$CH$_3$)$_3$]; 0.90t, 0.91t [9H; J=7.8 Hz; Si(CH$_2$C$\underline{H}_3$)$_3$]; 1.16d [3H; J=6.9 Hz; 21-H$_3$]; 1.54m [3H; 20-H$_3$]; 2.02m [2H, 3-H$_2$]; 2.21t [J=7.5 Hz; 2-H$_2$]; 2.67m [2H; 4-H$_2$]; 3.04m [1H; 8-H]; 3.32s [3H; OCH$_3$]; 3.59m [1H; 11-H]; 4.67m [1H; 9-H]; 6.08dd [1H; J=15.3,2.3 Hz; 14-H]; 6.78m [2H; 13-H, 2'-H]; 6.91m [2H; 1'-H, 3'-H] $^{13}$C NMR (100 MHz, $C_6D_6$), δC (ppm): 4.0 [C-20]; 5.7 [Si(C$\underline{H}_2$CH$_3$)$_3$]; 7.6 Si(CH$_2$C$\underline{H}_3$)$_3$]; 17.0 [C-21]; 23.2, 23.3 [C-17]; 26.0 [C-3]; 30.4 [C-4]; 34.2 [C-2]; 43.7 [C-10]; 45.2, 45.3 [C-16]; 50.3 [C-8]; 51.6 [OCH$_3$]; 59.6 [C-12]; 77.1 [C-11]; 77.8, 77.9, 78.0 [C-18, C-19]; 84.9 [C-9]; 121.6 [C-2']; 122.8 [C-3']; 124.5 [C-5]; 130.1 [C-1']; 130.4 [C-7]; 130.7 [C-14]; 146.8, 146.9 [C-13]; 158.6 [C-6]; 173.8 [C-1]; 200.5 [C-15].

EXAMPLE 4

The Compound of the General Formula (III)—wherein $R^2$ Stands for Methyl Group 1.2 g (2 mmol) of crude silyl-enone of the general formula (IV) obtained in the Example 3 is dissolved in 20 ml of methanol and 0.15 ml (1.8 mmol) of concentrated hydrochloric acid is added thereto. The mixture is stirred for 5 minutes at 25° C. and 0.16 g (1.9 mmol) of solid $NaHCO_3$ is added thereto. This mixture is stirred for 10 minutes at 25° C. and then it is evaporated in vacuum. The residue is dissolved in toluene, the inorganic salts are filtered off and the filtrate is evaporated. The crude product obtained is purified by column chromatography, and thus the above title compound is obtained as a yellow oil.

Yield: 0.46 g (56%)

TLC-$R_f$ (diisopropylether-ethylacetate-acetic acid 50:50:1.5)=0.50.

$^1$H NMR (400 MHz, $CDCl_3$), δH (ppm): 1.21d [1H, J=7.0 Hz; 21-$H_3$]; 1.77t [3H; J=2.0 Hz; 20-$H_3$]; 1.94m [2H; 3-$H_2$]; 2.08ddd [1H, J=13.6,8.4,5.0 Hz; 10-$H_b$]; 2.27m [1H, 17-$H_b$]; 2.33t [2H, J=7.5, Hz; 2-$H_2$]; 2.46m [1H, 17-$H_a$]; 2.62m [2H, 4-$H_2$]; 2.68m [2H, 10-$H_a$, 12-H]; 2.90sx [1H, J=7.0 Hz; 16-H1]; 3.58t [1H, J=8.5; 8-H]; 3.65s [3H; $OCH_3$]; 4.11m [1H; 11-H]; 5.16ddd [1H; J=8.5,7.2,5.0 Hz; 9-H]; 6.34d [1H, J=15.6; 14-H]; 6.78m [1H; 2'-H]; 6.89dd [1H; J=15.6,8.8 Hz; 13-H]; 6.94m, [2H; 1'-H, 3'-H] $^{13}$C NMR (100 MHz, $CDCl_3$), δC (ppm): 3.5 [C-20]; 16.4 [C-21]; 22.3 [C-17]; 24.7 [C-2]; 29.1 [C-4]; 33.4 [C-3]; 41.8 [C-10]; 44.1 [C-16]; 50.3 [C-8]; 51.5 [$OCH_3$]58.6 [C-12]; 76.4 [C-11]; 76.6, 77.2 [C-18, C-19]; 84.6 [C-9]; 120.7 [C-2']; 121.9 [C-3']; 123.5 [C-5]; 129.1, 129.2 [C-14, C-1']; 129.7 [C-7]; 146.0 [C-13]; 157.2 [C-6]; 174.1 [C-1]; 201.7 [C-15].

EXAMPLE 5

The Compound of the General Formula (II)—wherein $R^2$ Means Methyl Group 5.14 g (22 mmol) of 2,6-di-t-butyl-4-methylphenol is dissolved in 50 ml of distilled toluene under nitrogen atmosphere. 1.55 g (11 mmol) of diisobutyl-aluminiumhydride dissolved in 8 ml of distilled toluene is added dropwise to the above solution. The reaction mixture is stirred for one hour at 0° C., then it is cooled to −78° C. To this diisobutylaluminium-2,6-di-t-butyl-4-methylphenoxide reagent 0.45 g (1.1 mmol) of compound of the general formula (III) obtained in Example 4 dissolved in 4 ml distilled toluene is added slowly dropwise at −78° C. The reaction mixture is stirred for a night at −50° C. and then it is quenched with 27 ml of 2 M aqueous hydrochloric acid solution. After stirring for 30 minutes the phases are separated, the aqueous phase is washed twice with 15 ml of toluene, the combined organic phase is washed with 20 ml of saturated NaCl solution, 15 ml of 1 M aqueous solution of $NaHCO_3$ and with 2×20 ml of saturated NaCl solution. The organic phase is dried on $Na_2SO_4$ and it is evaporated in vacuum. The above title compound is obtained by purification using chromatography from the residue as a colourless oil.

Yield: 0.25 g (55%)

TLC-$R_f$ (diisopropyl-ether:ethylacetate:acetic acid 50:50:1.5)=0.24

TLC-$R_f$ (toluene:dioxan:acetic acid 20:10:1)=0.50

$^1$H NMR (400 MHz, $CDCl_3$), δH (ppm): 1.02t [3H; J=6.8 Hz; 21-$H_3$]; 1.79m [1H; 16-H]; 1.80t, 1.81t [3H; J=2.6 Hz 20-$H_3$]; 1.88–2.18m [6H; 3-$H_2$, 10-$H_b$, 17-$H_b$, OH]; 2.25m [1H; 17-$H_a$]; 2.33m [1H; 2-$H_2$]; 2.48m [1H; 12-H]; 2.61m, [2H; 4-$H_2$]; 2.66m [1H; 10-$H_a$]; 3.46t, 3.47t [1H; J=8.2 Hz 8-H]; 3.66s [3H; $OCH_3$]; 3.95m [1H; 11-H]; 4.07t, 4.21dd [1H; J=7.0, J=5.8, 4.9; 15-H]; 5.12m [1H; 9-H]; 5.63dd [1H; J=15.5, J=5.8, 7.0; 14-H]; 5.70dd, 5.71dd [1H; J=15.5, 8.4, J=15.5, 8.0; 13-H]; 6.77m [1H; 2'-H]; 6.97m [2H; 1'-H, 3'-H];

EXAMPLE 6

Beraprost of the Formula (I)

0.246 g (0.6 mmol) of compound of the general formula (II) obtained in Example 5 is dissolved in 1 ml of methanol and 1 ml of 1 M aqueous sodium hydroxide solution is added dropwise slowly thereto. After stirring for an hour the methanol is distilled off from the reaction mixture in vacuum. The aqueous residue is diluted with 10 ml of water extracted with methyl-tert.butyl-ether and the combined organic phase is washed with saturated NaCl solution, dried on $Na_2SO_4$ and evaporated. The residue of evaporation is crystallized from ethylacetate-hexane mixture and the pure above mentioned title compound is obtained as colourless crystals.

Yield: 0.21 g (87%)

TLC-$R_f$ (toluene-dioxan-acetic acid 20:10:1)=0.41

Melting point: 98–112° C.

$^1$H NMR (400 MHz, $CDCl_3$), δH (ppm): 1.00d, 1.03d [3H; J=6.8 Hz; 21-$H_3$]; 1.79m [1H; 16-H]; 1.80t, 1.81t [3H, J=2.5,2.4 Hz; 20-$H_3$]; 2.3–1.9m [5H, 3-$H_2$, 10$H_b$, 17-$H_2$]; 2.34t [1H; J=7.4 Hz; 2-$H_2$]; 2.43m [1H; 12-H]; 2.64m [3H; 10-$H_a$, 4-$H_2$]; 3.43t, 3.44t [1H, J=8.7,8.5 Hz; 8-H]; 3.92m [1H; 11-H]; 4.07t, 4.17t [1H, J=7.3,5.6 Hz; 15-H]; 4.3b [2H; OH]; 5.09m [1H, 9-H]; 5.58dd, 5.61dd [1H; J=15.3,6.5 Hz; 14-H]; 5.67dd, 5.68dd [1H; J=15.3,8.0 Hz; 13-H]; 6.77m [1H; 2'-H]; 6.95m [2H; 1'-H,3'-H] $^{13}$C NMR (100 MHz, $CDCl_3$), δC (ppm): 3.5, 3.6 [C-20]; 14.7, 15.8 [C-21]; 22.3, 22.6 [C-17]; 24.6 [C-2]; 29.1 [C-4]; 33.1 [C-3]; 38.2, 38.3 [C-16]; 41.2 [C-10]; 50.4 [C-8]; 58.8 [C-12]; 75.8, 76.3, 76.4 [C-11, C-15]; 77.2, 77.4 [C-18, C-19]; 84.5, 84.6 [C-9]; 120.6 [C-2']; 121.9 [C-3']; 123.2 [C-5]; 129.0 [C-1']; 129.7 [C-7]; 132.3, 133.0, 133.8, 134.0 [C-13, C-14]; 157.2 [C-6]; 178.3 [C-1].

EXAMPLE 7

Beraprost Sodium Salt (The Sodium Salt of the Compound of Formula (I)

0.199 g of beraprost is dissolved in 2 ml of methanol, 0.5 ml of 1 M aqueous solution of sodium hydroxide is added thereto and after their mixing the solvent is evaporated in vacuum and thus the above title salt is obtained as colourless crystals.

Yield: 0.21 g (100%)

Melting point: >205° C.

$^1$H NMR (400 MHz, DMSO-$d_6$), δH (ppm): 0.90d, 0.92d [3H; J=6.7 Hz; 21-$H_3$]; 1.75–1.55m [7H; 10$H_b$, 16-H, 3-$H_2$, 20-$H_3$]; 1.89t [2H, J=7.6 Hz; 2-$H_2$]; 1.94m [1H; 17-$H_b$]; 2.16q [1H, J=8.5 Hz; 12-H]; 2.25m [1H; 17-$H_a$]; 2.44t [2H; J=7.5 Hz; 4-$H_2$]; 2.50o [1H; 10-$H_a$]; 3.39t [1H, J=8.5 Hz; 8-H]; 3.72td [1H; J=8.5,6.1 Hz; 11-H]; 3.84t 3.96t [1H, J=6.5,6.0 Hz; 15-H]; 4.85b [2H, OH]; 5.01dt [1H, J=8.5,6.6 Hz; 9-H]; 5.46dd, 5.47dd [1H; J=15.4,6.5 Hz, J=15.4,6.0 Hz; 14-H]; 5.65dd, 5.66dd [1H; J=15.4,8.5 Hz; 13-H]; 6.71m [1H; 2'-H]; 6.92m [2H; 1'-H, 3'-H] During the above thin layer chromatography (TLC) procedures we used plates MERCK Kieselgel 60 F$_{254}$, thickness of layer is 0.2 mm, length of plates is 5 cm.

The invention claimed is:

1. A compound of formula (VI):

wherein R² is a straight or branched alkyl group containing 1–4 carbon atoms—and R¹ is a methyl or an ethyl group.

2. A compound of the general formula (VI):

wherein R¹ stands for ethyl group and R² stands for methyl group.

3. A compound of formula (V):

wherein R² is a straight or branched alkyl group containing 1–4 carbon atoms—and R¹ is a methyl or an ethyl group.

4. A compound of formula (V):

wherein R¹ stands for ethyl group and R² stands for methyl group.

5. A compound of formula (IV):

wherein R² is a straight or branched alkyl group containing 1–4 carbon atoms—and R¹ is a methyl or an ethyl group.

6. A compound of the general formula (IV):

wherein R¹ stands for ethyl group and R² stands for methyl group.

7. A process for the preparation of the compound of formula (I):

and salts thereof, which comprises:
(A) reacting a compound of formula (VII):

wherein $R^2$ is a straight or branched alkyl group containing 1–4 carbon atoms, with a compound of formula (VIII):

(VIII)

wherein $R^1$ is a methyl or an ethyl group, X is a chlorine, bromine or iodine atom,
$CF_3SO_2$—O-group, azido-, cyano-, or group or acetamido or acetyloxy, to obtain a compound of formula (VI):

wherein the meaning of $R^1$ and $R^2$ are as defined above;

(B) oxidizing the compound of Formula (VI) into the aldehyde of the formula (V):

wherein the meaning of $R^1$ and $R^2$ are as defined above;
(C) reacting the aldehyde of formula (V), with or without isolation, with a phosphonate of formula (IX)

wherein $R^3$ is a straight or branched alkyl group containing 1–4 carbon atoms to obtain the compound of formula (IV):

wherein the meaning of $R^1$ and $R^2$ are as defined above;
(D) deprotecting the compound of formula (IV) by splitting off the protecting group at the position 11 to obtain the compound of formula (III):

(III)

wherein the meaning of $R^2$ is as defined above;

(E) reducing the compound of formula (III) to obtain the compound of formula (II):

(II)

wherein the meaning of $R^2$ is as defined above;

(F) hydrolyzing the compound of formula (II) to obtain an acid of the formula (I); and either:

(G) (i) isolating the acid of the compound of formula (I);
(ii) reacting the isolated acid of the compound of formula (I) with a base to form a salt of the compound of formula (I); and
(ii) isolating the salt of the compound of formula (I); or (H) (i) reacting the acid of the compound of formula (I) with a base to form a salt of the compound of formula (I); and
(ii) isolating the salt of the compound of formula (I) thus obtained.

8. The process according to claim 7, wherein in the compound of formula (VIII), $R^1$ is ethyl and X is chlorine, bromine or iodine atom, cyano-, azido-, $CF_3SO_2$—O— or

9. The process according to claim 1, wherein the compound of formula (VI) is oxidized into a compound of formula (V) by using a mixture of dimethyl sulfoxide, oxalyl chloride and triethylamine.

10. The process according to claim 1, wherein an aldehyde of formula (V) and a phosphonate of formula (IX) are reacted in a Wittig-HornerEmmon's reaction.

11. The process according to claim 1, wherein the protecting group of the hydroxyl group at position 11 of the compound of formula (IV) is split off in the acidic medium.

12. The process according to claim 1, wherein the reduction of a compound of formula (III) is carried out with diisobutylaluminium-2,6-di-tert.butyl-4-methylphenoxide.

13. The process according to claim 1, wherein the compound of formula (II) is hydrolized in basic medium.

14. The process according to claim 1, wherein the acid of formula (I) is transformed into its sodium salt and that salt is isolated.

15. The process of claim 7, wherein the salt is a sodium salt of a compound of formula (I).

* * * * *